(12) United States Patent
Dong et al.

(10) Patent No.: US 7,761,162 B2
(45) Date of Patent: Jul. 20, 2010

(54) CAPTURE VERIFICATION WITH INTRINSIC RESPONSE DISCRIMINATION

(75) Inventors: Yanting Dong, Shoreview, MN (US); Scott A. Meyer, Rochester, MN (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 749 days.

(21) Appl. No.: 11/010,973

(22) Filed: Dec. 13, 2004

(65) Prior Publication Data

US 2006/0129196 A1 Jun. 15, 2006

(51) Int. Cl.
*A61N 1/365* (2006.01)

(52) U.S. Cl. ............................................. 607/28; 607/9
(58) Field of Classification Search .................... 607/28; 600/508
See application file for complete search history.

(56) References Cited

U.S. PATENT DOCUMENTS

| | | | |
|---|---|---|---|
| 3,920,005 A | 11/1975 | Gombrich et al. | |
| 4,878,497 A | 11/1989 | Callaghan et al. | |
| 5,222,493 A | 6/1993 | Sholder | |
| 5,271,411 A | 12/1993 | Ripley et al. | |
| 5,324,310 A | 6/1994 | Greeninger et al. | |
| 5,350,410 A | 9/1994 | Kleks et al. | |
| 5,431,693 A * | 7/1995 | Schroeppel | 607/28 |
| 5,443,485 A | 8/1995 | Housworth et al. | |
| 5,522,860 A | 6/1996 | Molin et al. | |
| 5,626,620 A | 5/1997 | Kieval et al. | |
| 5,683,431 A | 11/1997 | Wang | |
| 5,683,434 A | 11/1997 | Archer | |
| 6,101,416 A | 8/2000 | Sloman | |
| 6,128,535 A | 10/2000 | Maarse | |
| 6,148,234 A | 11/2000 | Struble | |
| 6,163,724 A | 12/2000 | Hemming et al. | |
| 6,169,921 B1 | 1/2001 | KenKnight et al. | |
| 6,175,766 B1 | 1/2001 | Bornzin et al. | |
| 6,192,275 B1 | 2/2001 | Zhu et al. | |
| 6,221,011 B1 | 4/2001 | Bardy | |

(Continued)

FOREIGN PATENT DOCUMENTS

EP 0468720 1/1992

(Continued)

OTHER PUBLICATIONS

Splett et al., Determination of Pacing Capture in Implantable Defibrillators: Benefit of Evoked Response Detection Using RV Coil to Can Vector, PACE, vol. 23, pp. 1645-1650, Nov. 23, 2000.

*Primary Examiner*—Carl H Layno
*Assistant Examiner*—Brian T Gedeon
(74) *Attorney, Agent, or Firm*—Hollingsworth & Funk, LLC

(57) ABSTRACT

Approaches to automatically classifying a cardiac response to pacing involve discriminating between a captured response and non-capture with intrinsic activation. A capture detection system senses for morphological characteristics of a cardiac signal associated with the pacing pulse. The cardiac signal may be sensed using a defibrillation electrode during one or more time intervals following delivery of the pacing pulse. If a first characteristic of the cardiac signal achieves a threshold value, the system continues to sense the cardiac signal and detects a second characteristic. The cardiac pacing response is determined based on at least one of the first and the second cardiac signal characteristics.

34 Claims, 13 Drawing Sheets

U.S. PATENT DOCUMENTS

| | | |
|---|---|---|
| 6,226,551 B1 | 5/2001 | Zhu et al. |
| 6,238,419 B1 | 5/2001 | Lindgren |
| 6,270,457 B1 | 8/2001 | Bardy |
| 6,275,731 B1 | 8/2001 | Zhu et al. |
| 6,277,072 B1 | 8/2001 | Bardy |
| 6,280,380 B1 | 8/2001 | Bardy |
| RE37,454 E | 11/2001 | Sutton et al. |
| 6,312,378 B1 | 11/2001 | Bardy |
| 6,324,427 B1 | 11/2001 | Florio |
| 6,336,903 B1 | 1/2002 | Bardy |
| 6,345,201 B1 | 2/2002 | Sloman et al. |
| 6,358,203 B2 | 3/2002 | Bardy |
| 6,368,284 B1 | 4/2002 | Bardy |
| 6,398,728 B1 | 6/2002 | Bardy |
| 6,434,428 B1 | 8/2002 | Sloman et al. |
| 6,440,066 B1 | 8/2002 | Bardy |
| 6,449,503 B1 | 9/2002 | Hsu |
| 6,456,881 B1 | 9/2002 | Bornzin et al. |
| 6,466,820 B1 | 10/2002 | Juran et al. |
| 6,477,422 B1 * | 11/2002 | Splett ............................. 607/28 |
| 6,493,586 B1 | 12/2002 | Stahmann et al. |
| 6,505,071 B1 | 1/2003 | Zhu et al. |
| 6,512,953 B2 | 1/2003 | Florio et al. |
| 6,567,701 B2 | 5/2003 | Vonk |
| 6,615,082 B1 | 9/2003 | Mandell |
| 6,618,619 B1 | 9/2003 | Florio et al. |
| 6,738,669 B1 | 5/2004 | Sloman et al. |
| 6,768,924 B2 | 7/2004 | Ding et al. |
| 6,950,702 B2 | 9/2005 | Sweeney |
| 6,973,350 B1 | 12/2005 | Levine et al. |
| 7,027,868 B2 | 4/2006 | Rueter et al. |
| 7,113,823 B2 | 9/2006 | Yonce et al. |
| 7,289,845 B2 * | 10/2007 | Sweeney et al. ............. 600/517 |
| 7,319,900 B2 * | 1/2008 | Kim et al. ....................... 607/27 |
| 7,330,761 B2 | 2/2008 | Zhang |
| 7,337,000 B2 | 2/2008 | Meyer et al. |
| 2001/0049542 A1 | 12/2001 | Florio et al. |
| 2002/0095188 A1 | 7/2002 | Mower |
| 2002/0138111 A1 | 9/2002 | Greenhut et al. |
| 2002/0183798 A1 | 12/2002 | Vonk |
| 2003/0050671 A1 | 3/2003 | Bradley |
| 2003/0083710 A1 | 5/2003 | Ternes et al. |
| 2003/0083711 A1 | 5/2003 | Yonce et al. |
| 2003/0204214 A1 | 10/2003 | Ferek-Patric |
| 2004/0082975 A1 | 4/2004 | Meyer et al. |
| 2004/0116971 A1 | 6/2004 | Bjorling et al. |
| 2004/0116974 A1 | 6/2004 | Obel |
| 2004/0127950 A1 | 7/2004 | Kim et al. |
| 2004/0127951 A1 | 7/2004 | Jarverud et al. |
| 2004/0171959 A1 | 9/2004 | Staler et al. |
| 2004/0215277 A1 | 10/2004 | Oosterhoff et al. |
| 2004/0243014 A1 | 12/2004 | Lee et al. |
| 2004/0260351 A1 | 12/2004 | Holmstrom et al. |
| 2005/0131476 A1 | 6/2005 | Kim et al. |
| 2005/0131477 A1 | 6/2005 | Meyer et al. |
| 2005/0131478 A1 | 6/2005 | Kim et al. |
| 2006/0241706 A1 | 10/2006 | Yonce et al. |
| 2006/0247693 A1 * | 11/2006 | Dong et al. ...................... 607/9 |
| 2006/0247695 A1 | 11/2006 | Stalsberg et al. |
| 2007/0016261 A1 | 1/2007 | Dong et al. |

FOREIGN PATENT DOCUMENTS

| | | |
|---|---|---|
| EP | 1291038 A2 | 3/2003 |
| EP | 1430930 | 6/2004 |
| WO | WO2004026398 | 4/2004 |

* cited by examiner

Figure 10B
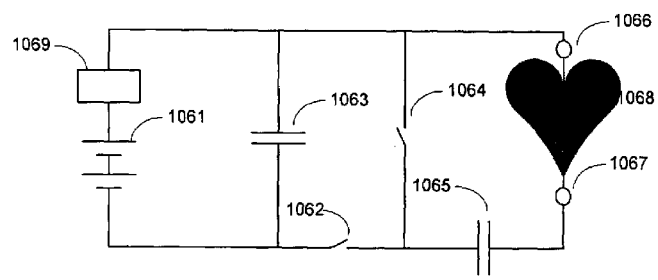
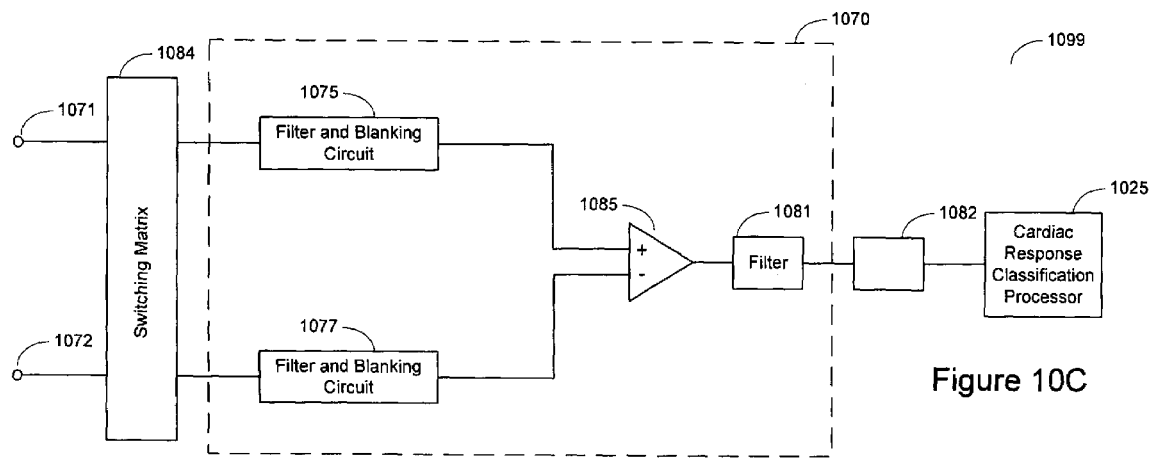
Figure 10C

CAPTURE VERIFICATION WITH INTRINSIC RESPONSE DISCRIMINATION

FIELD OF THE INVENTION

The present invention relates generally to implantable medical devices and, more particularly, to automatically classifying a cardiac response following delivery of a pacing pulse by the implantable device.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators have been used as an effective treatment for patients with serious arrhythmias. These systems typically comprise circuitry to sense electrical signals from the heart and a pulse generator for delivering electrical stimulation pulses to the heart. Leads extending into on, or near the patient's heart are connected to electrodes that electrically couple to the heart for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

Capture may be verified by detecting if a cardiac signal following a pace pulse indicates a captured response. However, the captured response must be discerned from other possible responses, including the superimposed residual post pace polarization without capture, and non-captured intrinsic beats.

SUMMARY OF THE INVENTION

The present invention involves methods and systems for classifying cardiac responses to pacing. One embodiment of the invention involves a method of classifying a cardiac response to a pacing pulse. The method involves sensing a cardiac signal associated with the pacing pulse and detecting morphological characteristics of the cardiac signal. Discrimination between a captured response and non-capture with intrinsic activity is performed based on at least one of the morphological characteristics.

In accordance with this one aspect of the invention, first characteristic and second morphological characteristics of the cardiac signal are detected. Following detection of a first morphological characteristic, sensing may continue if the first characteristic is consistent with a threshold value. During the continued sensing, a second characteristic is detected. The cardiac response to the pacing pulse is classified based on at least one of the first and the second cardiac signal characteristics. The cardiac response to the pacing pulse may be classified as non-capture if the first cardiac signal characteristic does not achieve the threshold criteria.

The cardiac signal may be sensed using a defibrillation electrode. Electrode combinations that may be used to sense the cardiac signal include a right ventricular tip/ring electrode and a right ventricular coil electrode, a left ventricular distal/proximal electrode and a left ventricular coil electrode, a right atrial tip/ring electrode and a superior vena-cava coil electrode, and/or a left atrial distal/proximal electrode and a left atrial coil electrode, for example.

The cardiac signal is sensed after a blanking period that follows the pacing pulse. A duration of the blanking period is selected to allow a pacing artifact signal component to dissipate from the sensed cardiac signal.

According to one aspect of the invention, the first cardiac signal characteristic is detected within a first time interval following the pacing pulse. The second cardiac signal characteristic is detected within a second time interval following the first time interval. The first cardiac signal characteristic may comprise a first peak value of the cardiac signal in the first time interval. The second cardiac signal characteristic may comprise a second peak value of the cardiac signal in the second time interval.

According to another aspect of the invention, a first peak value of the cardiac signal is compared to an average first peak value associated with captured response. The cardiac response may be classified as a non-captured response based on the comparison. At least one of the first peak value and a second peak value are compared to a value associated with a captured response. Discrimination between a captured response and a non-captured response with intrinsic cardiac activity may be performed based on the comparison. The average peak value associated with the captured response may be updated using an average peak value, e.g., a weighted average, of a plurality of cardiac signals representative of a captured cardiac response.

Another embodiment of the invention involves a capture detection system. The capture detection system includes a plurality of cardiac electrodes configured to electrically couple to a heart. A sensing system is coupled to the cardiac electrodes and is configured to sense a cardiac signal associated with a pacing pulse using the plurality of cardiac electrodes. A capture detector is coupled to the sensing system. The capture detector is configured to detect a first characteristic of the cardiac signal. The capture detector is further configured to detect a second characteristic of the cardiac signal if the first characteristic is consistent with a threshold criteria. The capture detector classifies the cardiac pacing response based on at least one of the first and the second characteristics.

According to one aspect of the invention, the capture detector is configured to sense the first characteristic of the cardiac signal in a first time interval and to sense the second characteristic of the cardiac signal in a second time interval. One or both of the first and second time intervals may be programmable.

The cardiac electrodes used to sense the cardiac signal may include a defibrillation electrode. For example, a right ventricular tip electrode and a right ventricular coil electrode, a left ventricular distal electrode and a left ventricular coil electrode, or a right atrial tip electrode and a superior venacava coil electrode may be used to sense the cardiac signal.

The sensing system may be blanked for a period of time following delivering of a pacing pulse. The duration of the blanking period may be selected to allow a majority of a pacing artifact signal component to dissipate from the sensed cardiac signal.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 10B is a schematic diagram of a circuit that may be used to generate pacing stimulations in accordance with embodiments of the invention; and FIG. 10C is a schematic diagram of a circuit that may be used to sense a cardiac signal following the delivery of a pacing stimulation and to classify the cardiac response to the pacing stimulation according to embodiments of the invention.

Figure 1A:
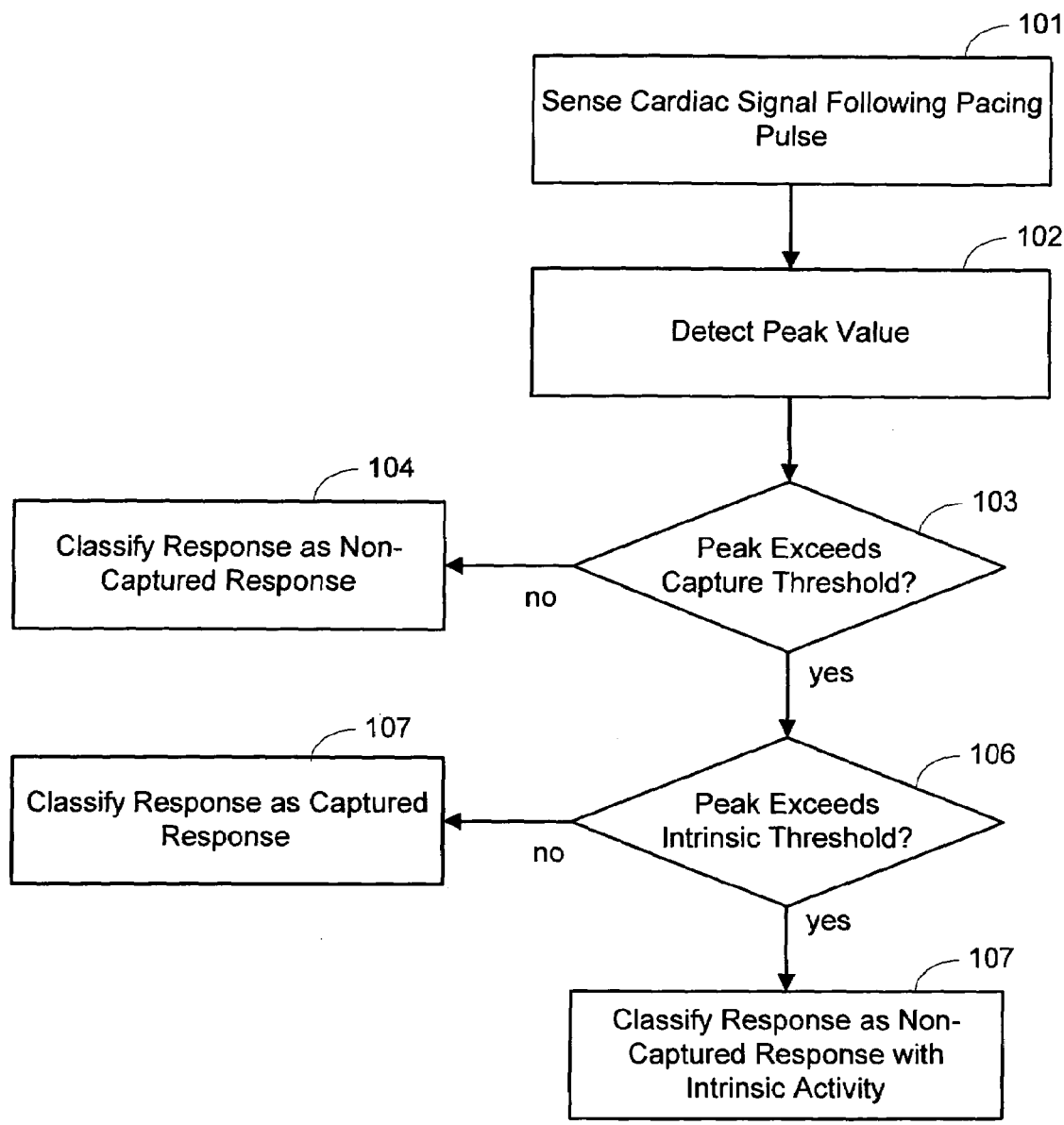
FIGS. 1A-1C are flowcharts illustrating methods for automatically classifying a cardiac response to a pacing pulse in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

When a pacing pulse delivered to a heart chamber produces a depolarization wave in cardiac tissue that results in a cardiac contraction, the captured response may be detected by examining the cardiac signal sensed in the heart chamber following the delivery of the pacing pulse. The present invention involves methods and systems for determining the cardiac response to pacing based on morphological characteristics of a cardiac signal sensed in a paced heart chamber after delivery of a pacing pulse. Embodiments of the invention are directed to systems and methods for discriminating between various possible cardiac responses following pacing, including a non-captured response, a captured response, and a non-captured response with intrinsic activity.

The flowchart of FIG. 1A illustrates a method of classifying the cardiac response to a pacing in accordance with embodiments of the invention. The method involves sensing 101 the cardiac signal associated with a pacing pulse following delivery of the pacing pulse. A peak value of the signal is detected 102. If the peak of the cardiac signal does not exceed 103 a capture threshold, then the cardiac response to the pacing pulse is classified 104 as a non-captured response. The threshold may comprise, for example, a fraction of a peak value associated with a captured response.

If the peak value of the cardiac signal exceeds 103 the capture threshold and remains below 106 an intrinsic activity threshold, then the cardiac response to pacing is classified 107 as a captured response. The intrinsic activity threshold may comprise, for example, a multiple of a peak value associated with a captured response. If the peak of the cardiac signal exceeds 106 the intrinsic response threshold, then the cardiac response is classified 108 as a non-captured response with intrinsic activity.

Figure 1B:
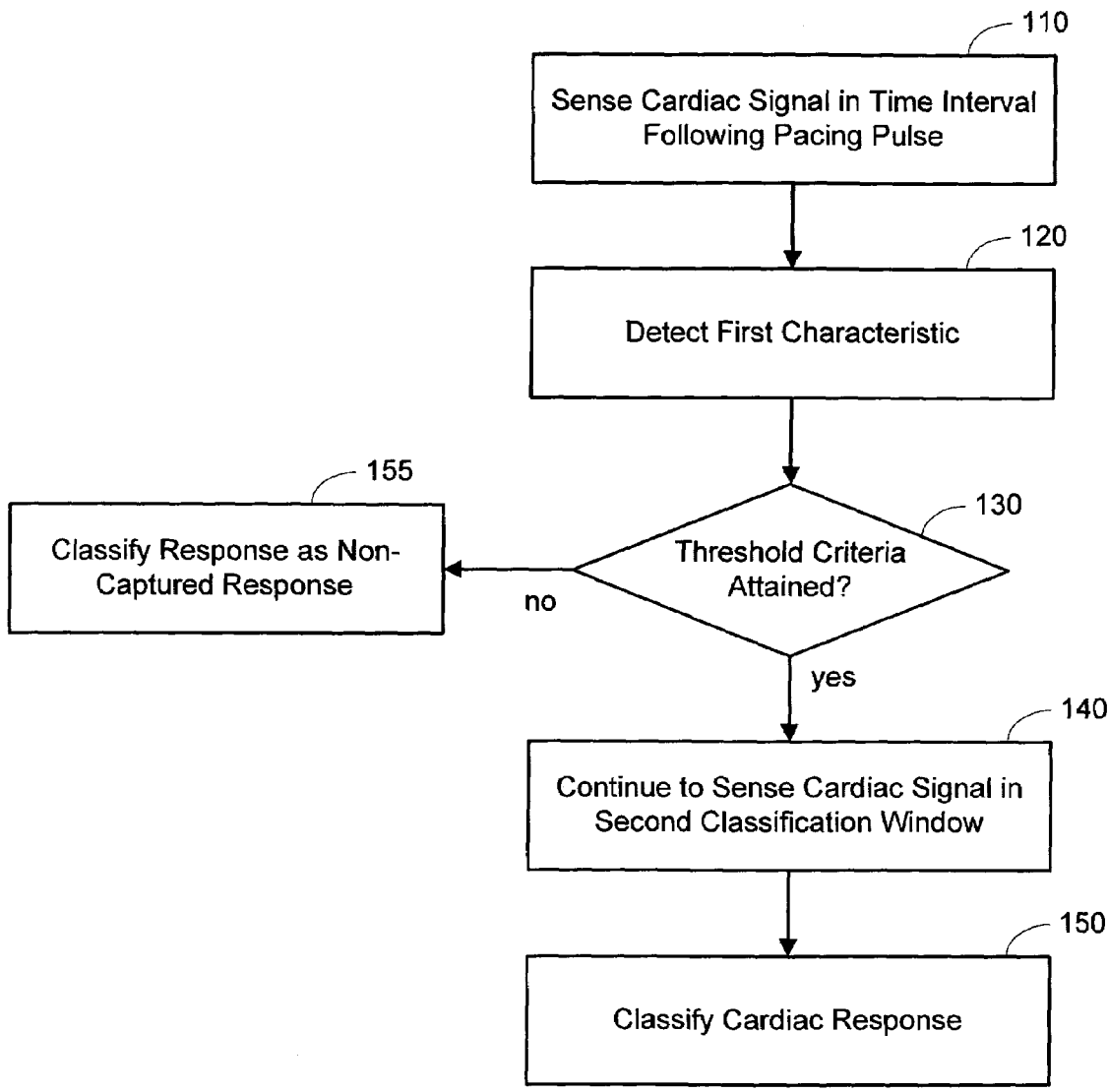

Another methodology of the invention is illustrated by the flowchart of FIG. 1B. The method involves sensing 110 the cardiac signal of the paced cardiac chamber in a first classification time interval following delivery of the pacing pulse. A characteristic of the cardiac signal is detected 120 in the first classification time interval. If the detected characteristic of the cardiac signal is not consistent with 130 a threshold criterion, then the cardiac response to the pacing pulse is classified 155 as a non-captured response. If the first characteristic is consistent with 130 the threshold criterion, then the system continues to sense 140 the cardiac signal in a second time interval. The cardiac response to the pacing stimulation is classified 150 based on at least one of the cardiac signal sensed in the first classification time interval and the cardiac signal sensed in the second classification time interval.

In accordance with the embodiments presented herein the cardiac signal sensed for cardiac response classification may include a defibrillation electrode. The cardiac response classification processes of the present invention may utilize any sensing vector that includes a near-field electrode, e.g., tip electrode, and a far-field electrode, e.g., coil electrode. In various implementations, a right ventricular signal of sufficient amplitude for cardiac response determination may be detected using a right ventricular tip/ring to right ventricular coil sensing vector; a right atrial signal of sufficient amplitude for cardiac response determination may be detected using a right atrial tip/ring to superior vena-cava coil sensing vector; a left ventricular signal of sufficient amplitude for cardiac response determination may be detected using a left ventricular distal/proximal electrode to left ventricular coil sensing vector; a left atrial signal of sufficient amplitude for cardiac response determination may be detected using a left atrial distal/proximal electrode to left atrial coil sensing vector.

Sensing for capture determination may follow a blanking interval, which may be programmable. In one embodiment, the blanking period immediately follows the pacing pulse and has a duration of about 45 ms. This blanking interval duration supports a wide range of pacing channel coupling capacitor values, and no special coupling capacitor is required for capture determination. The duration of the blanking period may be selected, for example, to allow the pacing artifact to dissipate while retaining adequate cardiac signal strength to determine the cardiac response to the pacing pulse.

After the blanking period, the system senses the cardiac signal associated with the pacing pulse and analyzes the sensed cardiac signal to discern the response to pacing. The use of a defibrillation coil, e.g., right ventricular (RV) coil, for sensing the cardiac signal following the pacing pulse enhances the ability to discern the cardiac response to pacing. The enhanced sensing performance of the coil is likely associated with the relatively large surface area of the coil and better contact of the coil with the myocardium when compared to smaller electrodes. Further, due to the spatial distance between the coil and the pacing electrode, e.g. RV tip electrode, the signal at the coil is slightly delayed allowing dissipation of the pacing artifact. The time delay and the enhanced sensing ability of the coil increases the signal level present on the coil electrode following the blanking period, improving the capture beat detection. The tip electrode, with its small surface area, is more sensitive to local cardiac activities, e.g. intrinsic activities, and provides a good sensing electrode for intrinsic activity detection. Therefore, the use of tip to coil sensing vector results in a good combination for detecting non-capture, capture, non-capture with intrinsic activities.

Within a first time interval following pacing, the system may detect a first characteristic comprising a morphological feature of the cardiac signal. In one implementation, the first characteristic is a peak value of the cardiac signal. In another implementation the first characteristic may comprise a peak width. Other morphological features may additionally or alternatively be utilized, such as the slope of the cardiac signal, the curvature of the cardiac signal, the timing of a particular feature of the cardiac signal or the relative timing of two or more features, a sequence of feature points, and/or other characteristic morphological features of the cardiac signal.

If the first characteristic is consistent with threshold value, a second characteristic of the cardiac signal sensed in a second time interval may be checked. The cardiac response to pacing may be classified based on at least one of the first characteristic and the second characteristic. The second characteristic may comprises any of the morphological features of the cardiac signal as listed above or other features. The second characteristic may be the same type of feature as the first characteristic, or a different type. For example, in one embodiment both the first and the second characteristics comprise a peak of the cardiac signal. In another example, the first characteristic may comprise a first feature type, e.g., a peak, and the second characteristic may comprise a second feature type, e.g., peak width. Various methods and systems involving cardiac response determination based on morphological characteristics of the cardiac signal associated with a pacing pulse are described in commonly owned U.S. Pat. No. 7,319,900 and U.S. Publication No. 2005/0131477, which are incorporated herein by reference.

Figure 1C:
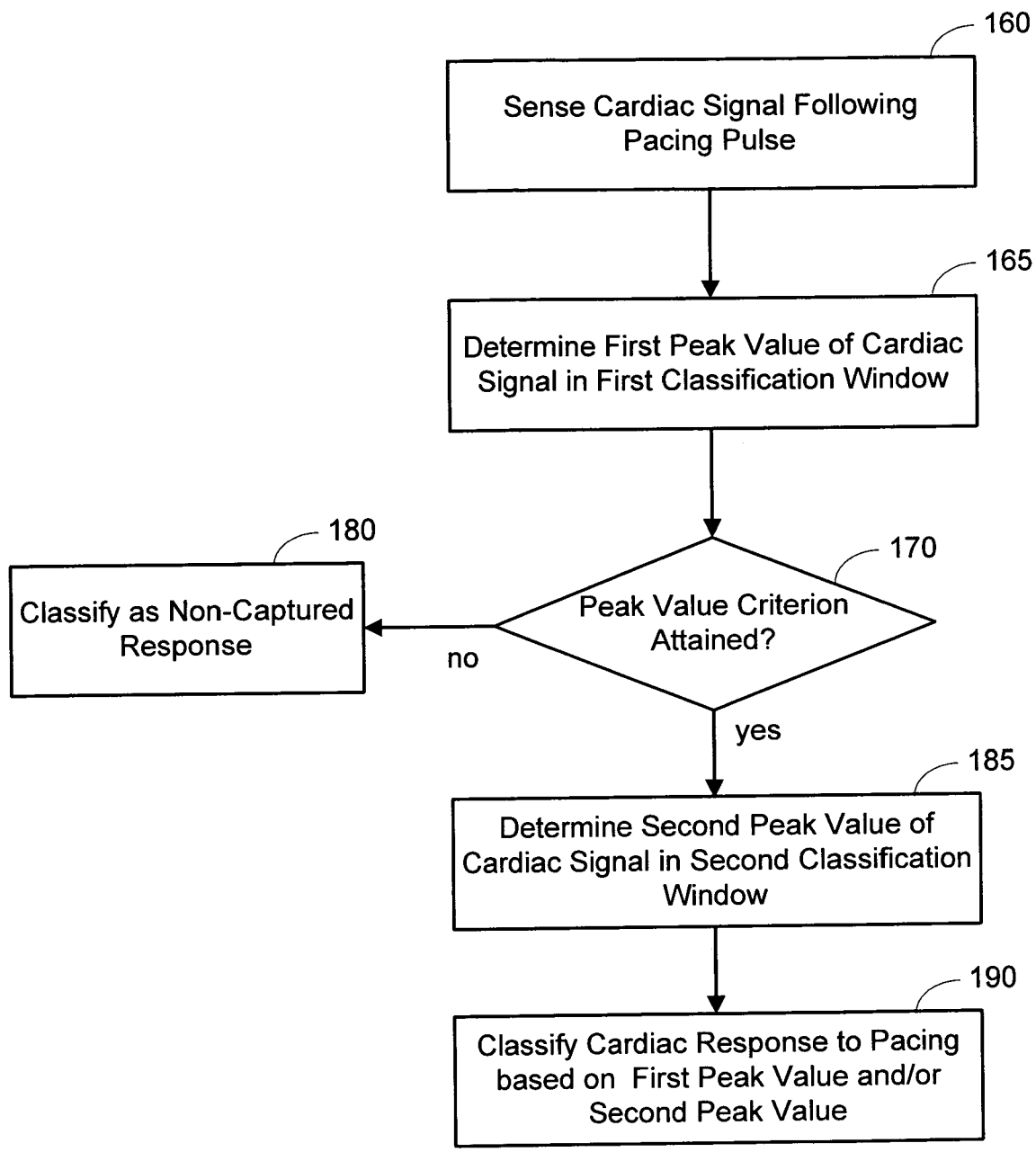

In one implementation, illustrated by the flow chart of FIG. 1C, the first characteristic comprises a peak value of the cardiac signal detected in a first time interval following the pacing pulse. After delivery of the pacing pulse the cardiac signal associated with the pacing pulse is sensed 160 following a blanking period. A first positive peak value of the cardiac signal in a first time interval is determined 165. If the first positive peak value does not reach 170 a threshold value, then the cardiac response is determined 180 to be a non-capture response. If the first positive peak value of the cardiac signal reaches 170 the threshold value, then a second positive peak value of the cardiac signal in a second time interval is determined 185. The cardiac response to pacing is determined 190 based on one or both of the first positive peak value and the second positive peak value. The cardiac response may be determined to be one of a captured response, a non-captured response, and a non-captured response and intrinsic beat.

Figure 2:
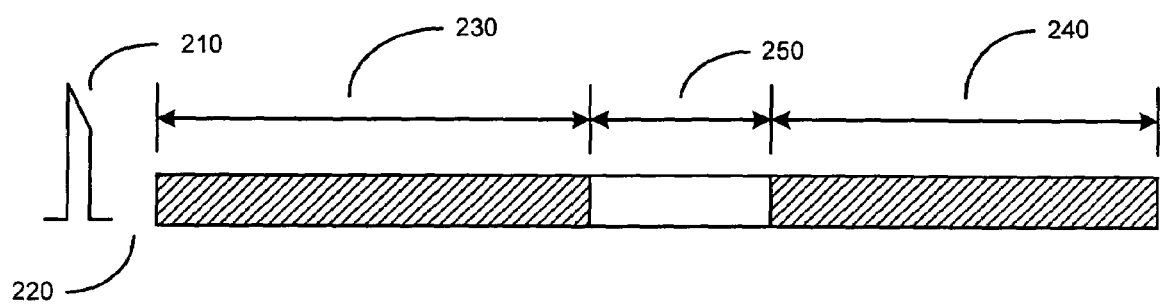
FIG. 2 illustrates time intervals that may be used in connection with the cardiac response classification methods and systems described in accordance with embodiments of the invention.

FIG. 2 illustrates time intervals that may be used in connection with the cardiac response classification methods and systems described herein. A pacing stimulation 210 is delivered to the heart, for example, to the right ventricle. The cardiac signal is blanked for a period of time 220 following pacing. Blanking may be accomplished by disconnecting the input to the sense amplifier or by otherwise rendering the sensing channel non-operational for a period of time 220. The blanking interval 220 may be programmable and may extend for example, from about 0 ms to about 45 ms following delivery of the pacing stimulation 210.

After the blanking period 220, a first classification interval 230 begins. The duration of the first classification interval may be less than about 325 ms, and may be programmable. The cardiac signal following the pacing pulse is sensed during the first time interval 230. If a first characteristic of the cardiac signal detected within the first time interval does not attain a threshold criterion, then the cardiac response to the pacing stimulation 210 is determined to be non-capture.

If the first characteristic attains the threshold criterion, then sensing continues in a second classification interval 240. The duration of the second classification interval 240 may be programmable, and may be less than about 325 ms. The duration of the second classification interval 240 may be different from that of the first classification interval 230. Alternatively, the lengths of the first and the second time intervals 230, 240 may be the same. The cardiac response to the pacing stimulation 210 is classified based on characteristics of the cardiac signal sensed in at least one of the first and the second time intervals.

A delay period 250 may occur between the end of the first classification interval 230 and the beginning of the second classification interval 240. The length of the delay may be fixed or programmable and may be in a range of about 0 ms (no delay) to about 40 ms, for example.

Figure 3:
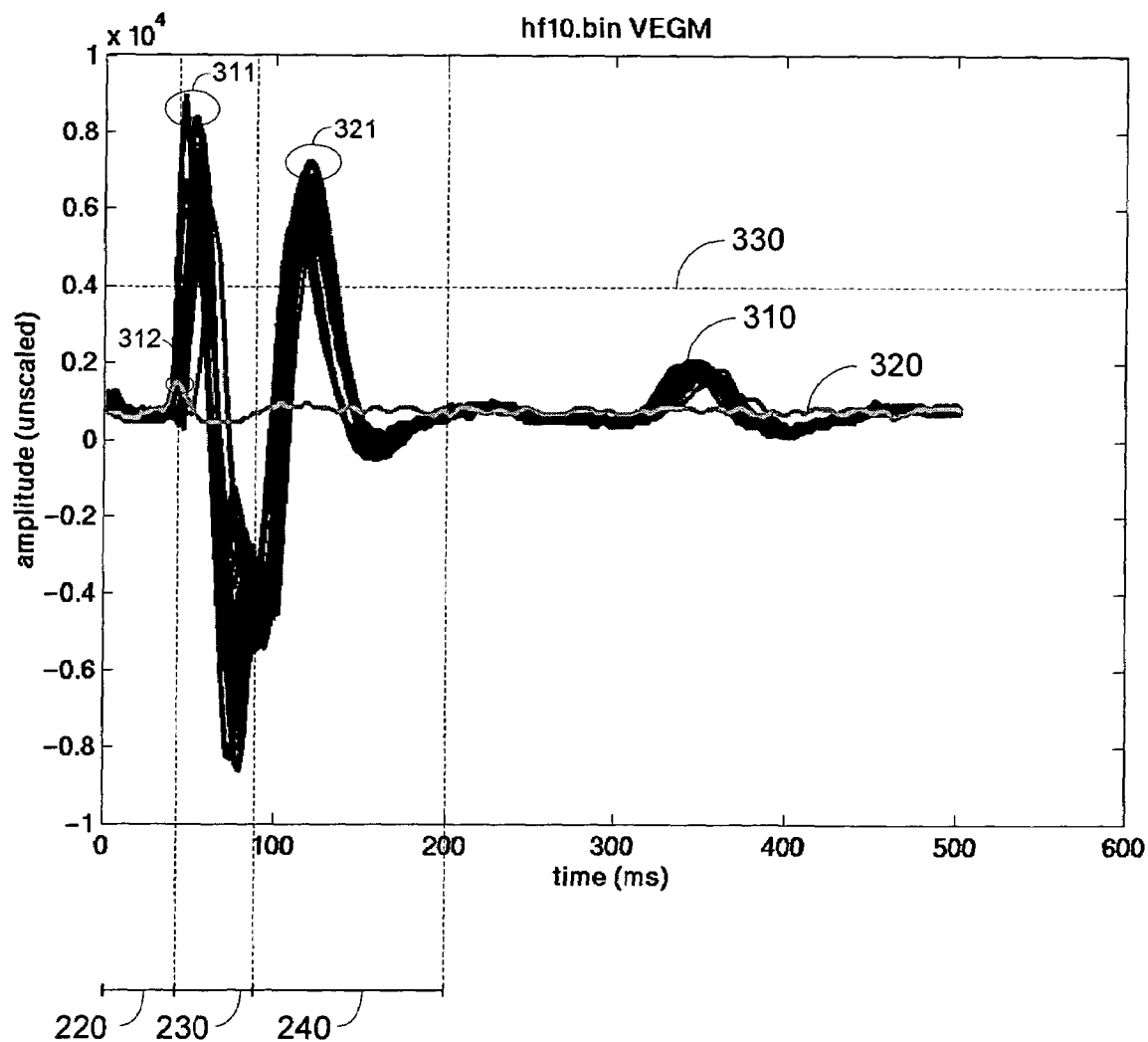
FIG. 3 graphically depicts how the morphologies of cardiac signals representative of a captured response and cardiac signals representative of a non-captured response can be utilized for cardiac response classification in accordance with embodiments of the invention.

FIG. 3 graphically illustrates the methods described above using the time intervals of FIG. 2. FIG. 3 depicts a number of cardiac signals 310 representative of a captured response superimposed on a cardiac signal 320 representative of a non-captured response. In this implementation, the system is blanked for a blanking period 220 of about 40 ms following a pacing pulse. The cardiac signal 310, 320 is sensed during a first classification interval 230. The positive peak value 311, 312 of the cardiac signal in the first classification interval 230 is detected. If the first positive peak value 312 does not attain a threshold value 330, then the cardiac response is determined to be non-capture.

Figure 4:
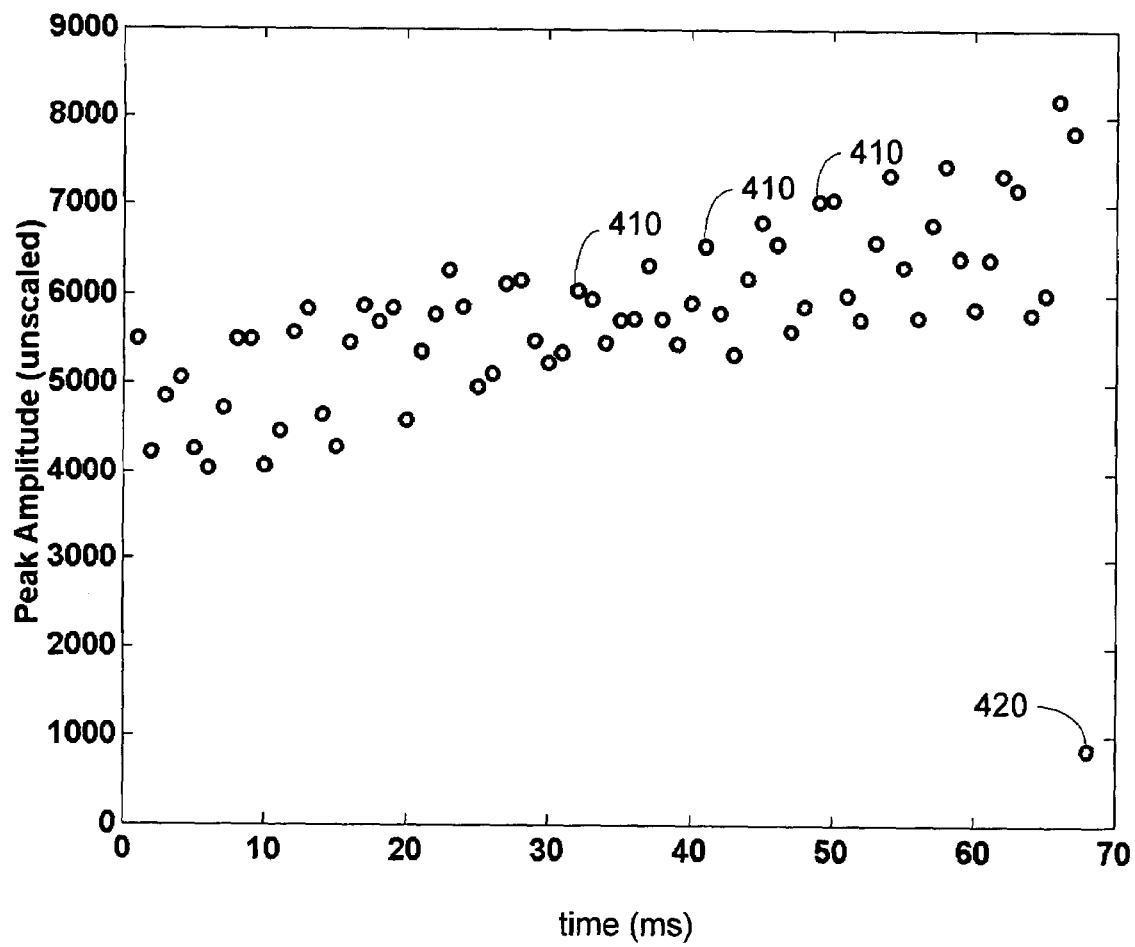
FIG. 4 is a diagram comparing peak values representative of captured responses to a peak value representative of a non-captured response, illustrating how morphological characteristics of the cardiac signals representative of captured responses and non-captured responses can be used to classify the cardiac response to pacing in accordance with embodiments of the invention.

If the first positive peak value 311, attains the threshold value 330, then the system senses for a second peak 321 of the cardiac signal 310 in the second classification interval 240. The cardiac response is determined based on at least one of the first 311 and the second 321 positive peak values. FIG. 4 illustrates the first peak values of a number of captured responses 410 compared to a first peak value representative of a non-captured response 420.

Various embodiments are directed to discriminating between a non-captured response (without intrinsic activity), a captured response, and non-captured response with intrinsic activity.

Figure 5:
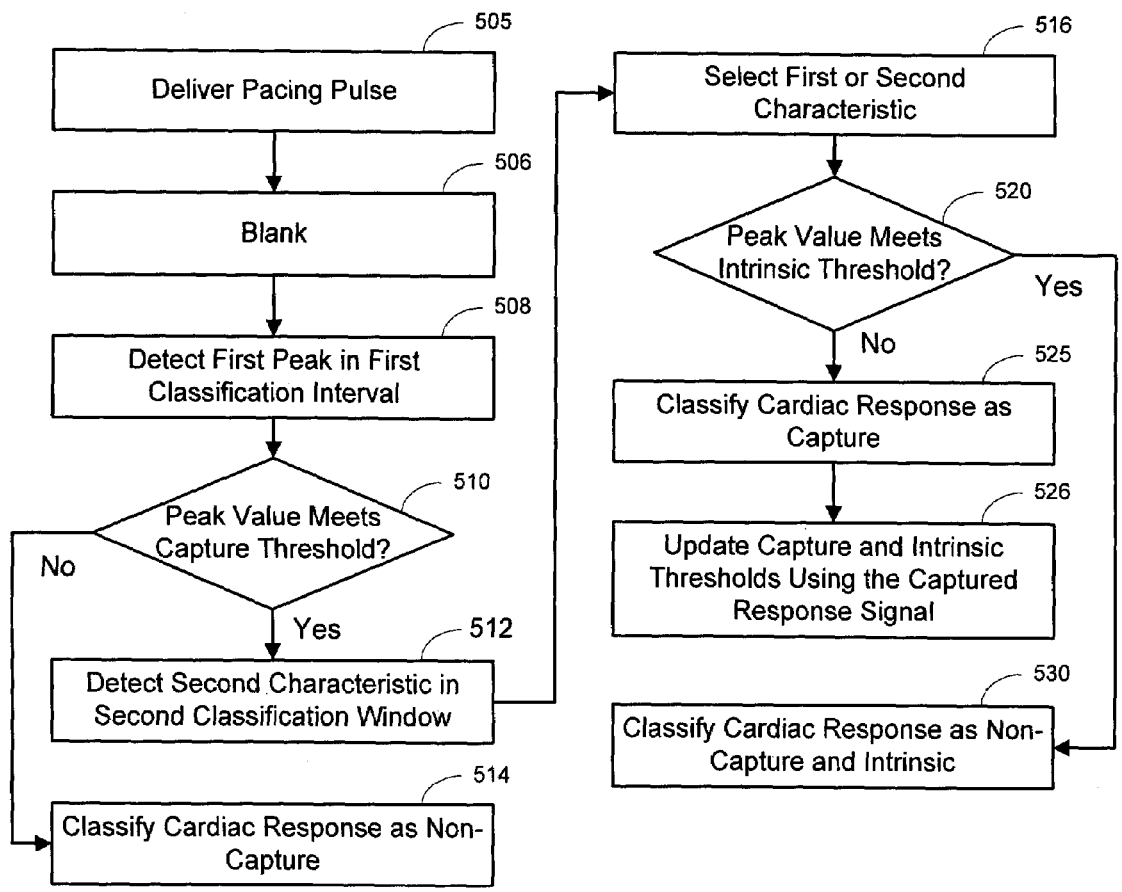
FIG. 5 is a flowchart depicting a method of determining the cardiac response to pacing using characteristic features of the cardiac electrical activity signal in the paced chamber in accordance with embodiments of the invention.

The flowchart of FIG. 5 depicts a method of determining the cardiac response to pacing using characteristic features of the cardiac electrical activity signal in the paced chamber. In this example, peak values of the cardiac signal are used to discriminate between various types of cardiac pacing responses. Other morphological characteristics may alternatively or additionally be used to determine the pacing response. For example, the morphological characteristic of the cardiac signal used to determine the cardiac pacing response may include, peak width, slope, curvature, feature timing, and/or other morphological characteristics or combinations of characteristics as previously discussed.

In accordance with this embodiment, peak values of the cardiac signal associated with a pacing pulse are used to classify the cardiac response to pacing as non-capture without intrinsic activity, capture, and non-capture with intrinsic activation. A non-captured response without intrinsic activity produces a cardiac signal having a relatively smaller peak amplitude when compared to a captured response or a non-captured response with intrinsic activity. A non-captured response with intrinsic activity produces a cardiac signal having a relatively larger peak amplitude when compared to a captured response or a non-captured response without intrinsic activation.

A method utilizing morphological characteristics of the cardiac signal following a pacing pulse to classify the cardiac response to pacing is illustrated in the flowchart of FIG. 5. A pacing pulse is delivered 505 to a cardiac chamber, e.g., the right ventricular chamber. Following a blanking interval 506, the cardiac signal is sensed and a cardiac signal peak is detected 508 in a first time interval following the pacing pulse.

If the cardiac signal peak detected in the first time interval does not reach 510 a capture threshold value, then the cardiac response to the pacing pulse is classified 514 as a non-captured response without intrinsic activity. If the cardiac signal peak detected in the first time interval reaches or exceeds 510 the capture threshold value, then the system detects 512 a second cardiac signal peak.

Either the first or the second detected peak value is selected 516 for comparison with an intrinsic threshold. If the selected peak value of the cardiac signal does not reach 520 the intrinsic threshold, then the cardiac response to the pacing pulse is determined 525 to be a captured response. The capture threshold and the intrinsic threshold are updated 526 using the captured cardiac signal. If the selected peak value reaches or exceeds 520 the intrinsic threshold, then the cardiac response to the pacing pulse is determined 530 to be a non-captured response with intrinsic activity.

Figure 6:
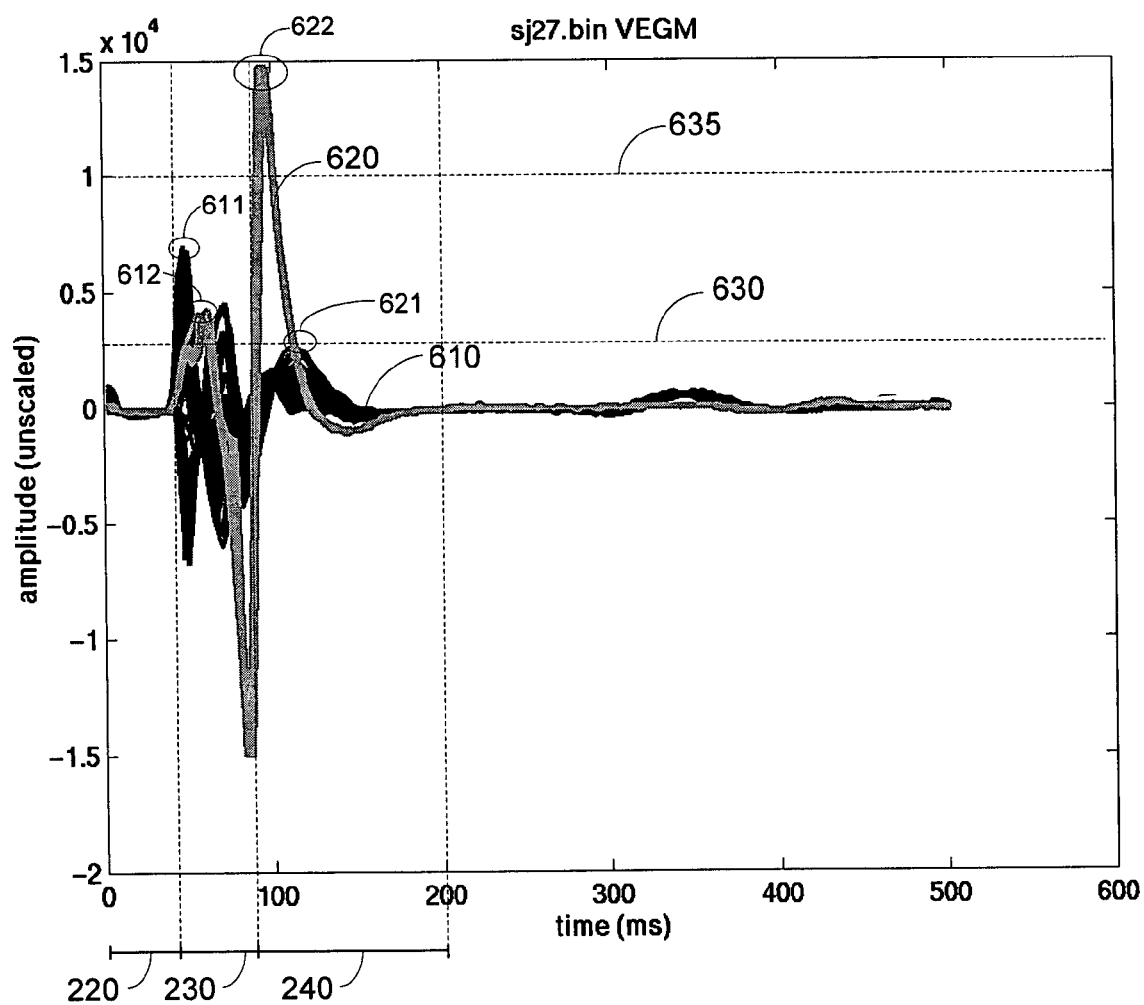
FIG. 6 graphically depicts how the morphologies of cardiac signals representative of a captured response and cardiac signals representative of a non-captured response with intrinsic activity can be utilized for cardiac response classification in accordance with embodiments of the invention.
Figure 7:
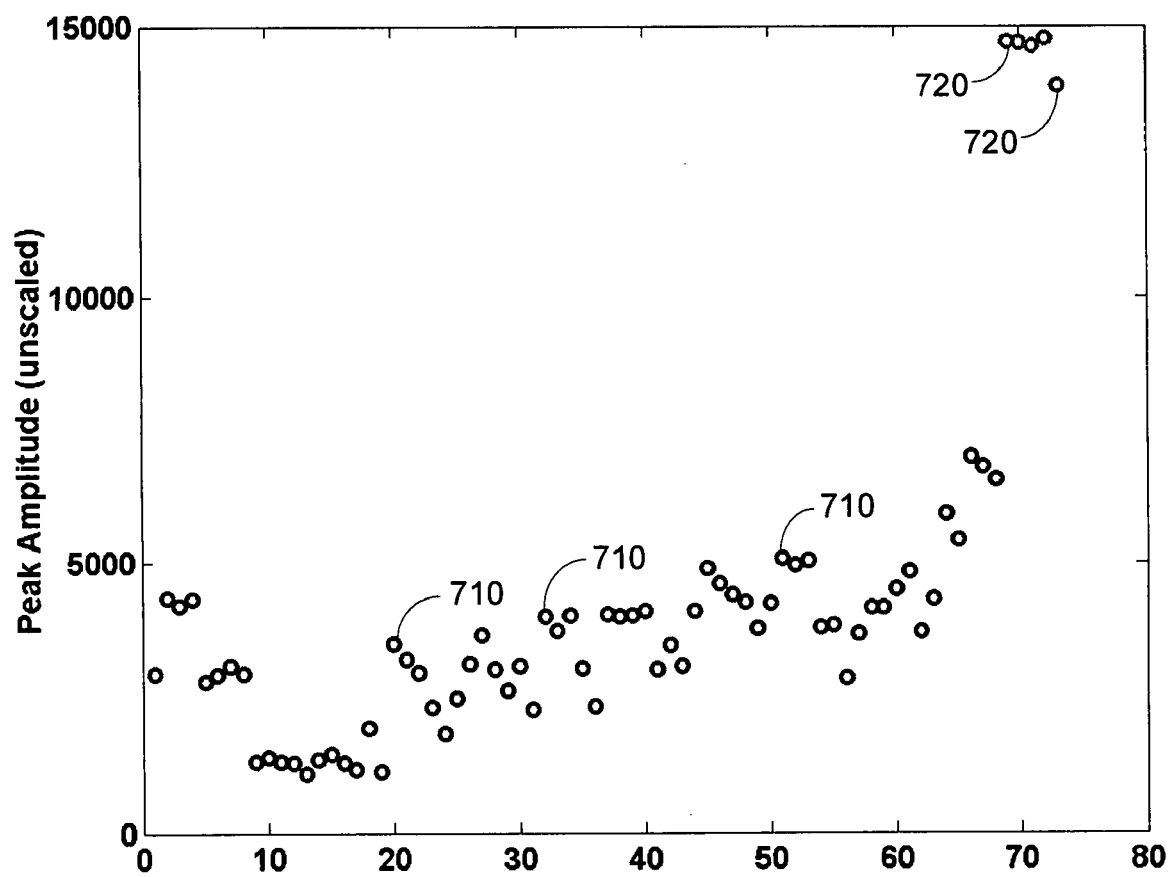
FIG. 7 is a diagram comparing peak values representative of captured responses to a peak values representative of a non-captured response with intrinsic activity, illustrating how morphological characteristics of the cardiac signals representative of captured responses and non-captured responses with intrinsic activity can be used to classify the cardiac response to pacing in accordance with embodiments of the invention.

FIGS. 6 and 7 graphically illustrate classification of the cardiac response to pacing as one of a captured response, and a non-captured response with intrinsic activity. In the example illustrated in FIGS. 6 and 7, positive peak values of the cardiac signal are used to determine the cardiac response to the pacing pulse. FIG. 7 illustrates maximum positive peak values 710 of a number of captured responses compared to maximum positive peak values 720 representative of a non-captured response with intrinsic activity. The positive peak values 720 of cardiac signals representing a non-captured response with intrinsic activity are relatively larger than the positive peak values 710 of cardiac signals representing a captured response.

FIG. 6 depicts a number of cardiac signals 610 representative of a captured response superimposed on a number of cardiac signals 620 representative of a non-captured response with intrinsic activity. The sensing system is blanked for a blanking period 220 of about 40-45 ms following a pacing pulse. First considering the captured response signals 610, the cardiac signal 610 is sensed during a first classification interval 230. The first positive peak value 611 of the cardiac signal 610 in the first classification interval 230 is determined. The first positive peak value 611, exceeds the capture threshold value 630, and the system continues to sense for the cardiac signal peak 621 in a second classification interval 240.

If the maximum of positive peaks 611 and 621 of the cardiac signal 610 does not reach the intrinsic response threshold value 635, then the cardiac response to the pacing pulse is classified as a captured response.

Next, the signals 620 representing a non-captured response with intrinsic activity are considered. The first positive peak value 612 is detected in the first classification interval 230. The first positive peak value 612 is determined to be larger than the captured response threshold 630, and the system continues to sense for the cardiac signal positive peak 622 in the second classification interval. 240. The maximum of detected positive peaks 612 and 622 exceed the intrinsic response threshold 635 and the cardiac response to the pacing pulse is classified as a non-captured, intrinsic beat.

Figure 8:
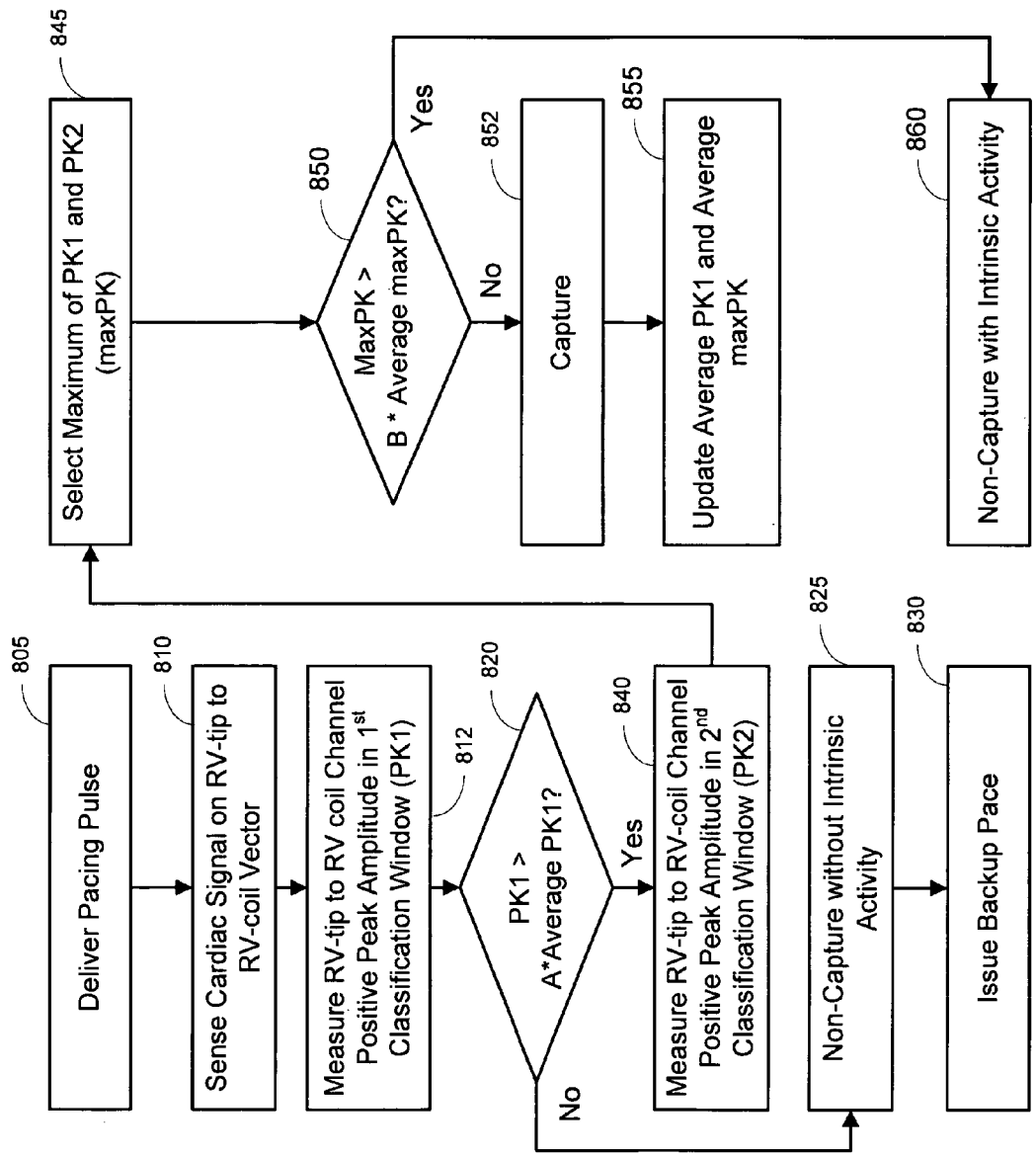
FIG. 8 is a flowchart illustrating a method of determining the cardiac response to pacing based on peak amplitudes of the cardiac signal detected in the first and/or second time intervals in accordance with embodiments of the invention.

The flowchart of FIG. 8 illustrates a method of determining the cardiac response to pacing based on peak amplitudes of the cardiac signal detected in the first and/or second time intervals, with right ventricle as an example. In this embodiment, a pacing pulse is delivered 805 to the right ventricle. Following a blanking interval, the cardiac signal following a pacing pulse is sensed 810 on the right ventricular (RV) tip to RV-coil vector. The positive peak (PK1) of the cardiac signal in the first classification time interval is determined 812 and is compared 820 to a capture threshold for discriminating between a captured response and a non-captured response. For example, the capture threshold may be a predetermined percentage of the average peak amplitude (average PK1) of captured response signals sensed on the RV-tip to RV-coil vector in the first classification interval. Thus, the capture threshold may comprise 40%, or another percentage, of the captured response average peak amplitude sensed in the first classification interval as expressed below in Equation 1:

$$\text{Capture Threshold} = A * \text{Average } PK1. \quad [1]$$

In one example, A=0.4. If the positive peak (PK1) of cardiac signal sensed on the RV-tip to RV-coil channel in the first classification interval is less than 820 the threshold criterion, then the cardiac response to pacing is classified 825 as a non-captured response without intrinsic activity. If the process is utilized in a beat to beat automatic capture verification process, a back up pace may be delivered 830.

If the peak (PK1) of the cardiac signal is greater than or equal to 820 the capture threshold, then the positive peak (PK2) of the cardiac signal in the second classification interval is determined 840. The maximum of PK1 and PK2, denoted maxPK is selected 845 and is compared 850 to the intrinsic threshold.

In the implementation illustrated in FIG. 8, the intrinsic threshold comprises a predetermined multiple of the average maximum peak amplitude of captured responses sensed in the first and second time intervals. For example, the intrinsic threshold may comprise twice the average maximum peak amplitude (average maxPK) of the captured response signals sensed in the first or second time intervals as expressed below in Equation 2:

$$\text{Intrinsic Threshold} = B * \text{Average max} PK \quad [2]$$

In one example, B=2. If the maximum of PK1 and PK2 is greater than 850 the intrinsic threshold, then the cardiac response to pacing is determined 860 to comprise a non-captured response with intrinsic activity.

If the cardiac signal is determined to be a captured response 852, the capture threshold and/or the intrinsic threshold may be updated 855. For example, capture threshold may be updated by recalculating the captured response average peak value (average PK1) in the first time interval using the current cardiac signal peak value in the first time interval as follows:

$$\text{Average } PK1_{(new)} = (1-c) * \text{Average } PK1_{(old)} + c * \text{Positive } PK1, \quad [3]$$

where Average $PK1_{(new)}$ is the updated average peak value sensed in the first time interval, Average $PK1_{(old)}$ is the previous average peak value sensed in the first time interval, Positive PK1 is the positive peak value of the current cardiac signal, and c is a constant. In one example, c=0.3.

The intrinsic threshold may be updated by recalculating the captured response average maximum positive peak value (average PK) using the current cardiac signal maximum peak value as follows:

$$\text{Average } PK_{(new)} = (1-c) * \text{Average } PK_{(old)} + c * PK, \quad [4]$$

Where Average $PK_{(new)}$ is the updated average maximum peak value of a captured response signal, Average $PK_{(old)}$ is the previous average maximum peak value, PK is the maximum peak value of the current cardiac signal, and c is a constant. In one example, c=0.3.

By way of example, the processes of the present invention may be used to enhance capture threshold testing to determine the optimal energy for pacing. Determination of the optimal pacing energy may be implemented, for example, by an automatic capture threshold testing procedure executed by an implantable cardiac rhythm management system. Additionally, automatic capture verification may be used to monitor pacing on a beat-by-beat basis. Automatic capture verification may be used to control back up pacing when a pace pulse delivered to the heart fails to evoke a captured response (CR). These and other applications may be enhanced by employment of the systems and methods of the present invention.

Those skilled in the art will appreciate that reference to a capture threshold procedure indicates a method of determining the capture threshold in one of left atrium, right atrium, left ventricle, and right ventricle. In such a procedure, the pacemaker, automatically or upon command, initiates a search for the capture threshold of the selected heart chamber. The capture threshold comprises the lowest pacing energy that consistently captures the heart.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern, or other pattern.

Automatic capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 70-80 ms after the initial pace pulse. The pacemaker may adjust the pacing energy if a pacing pulse does not capture the heart. If a predetermined number of pacing pulses delivered during normal pacing do not produce a captured response, the pacemaker may initiate a capture threshold test to determine the capture threshold. Automatic capture detection and back up pacing may be implemented using the cardiac response classification processes of the present invention.

The embodiments of the present system are generally described herein as being implementable in an implantable cardiac defibrillator (ICD) that may operate in numerous pacing modes known in the art. Various types of single and multiple chamber implantable cardiac defibrillators are known in the art and may be used in connection with the cardiac response classification methods of the present invention. The methods of the present invention may be implemented in a variety of implantable or patient-external cardiac rhythm management devices, including single and multi-chamber pacemakers, defibrillators, cardioverters, rate adaptive pacemakers, bi-ventricular pacemakers, and cardiac resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 9:
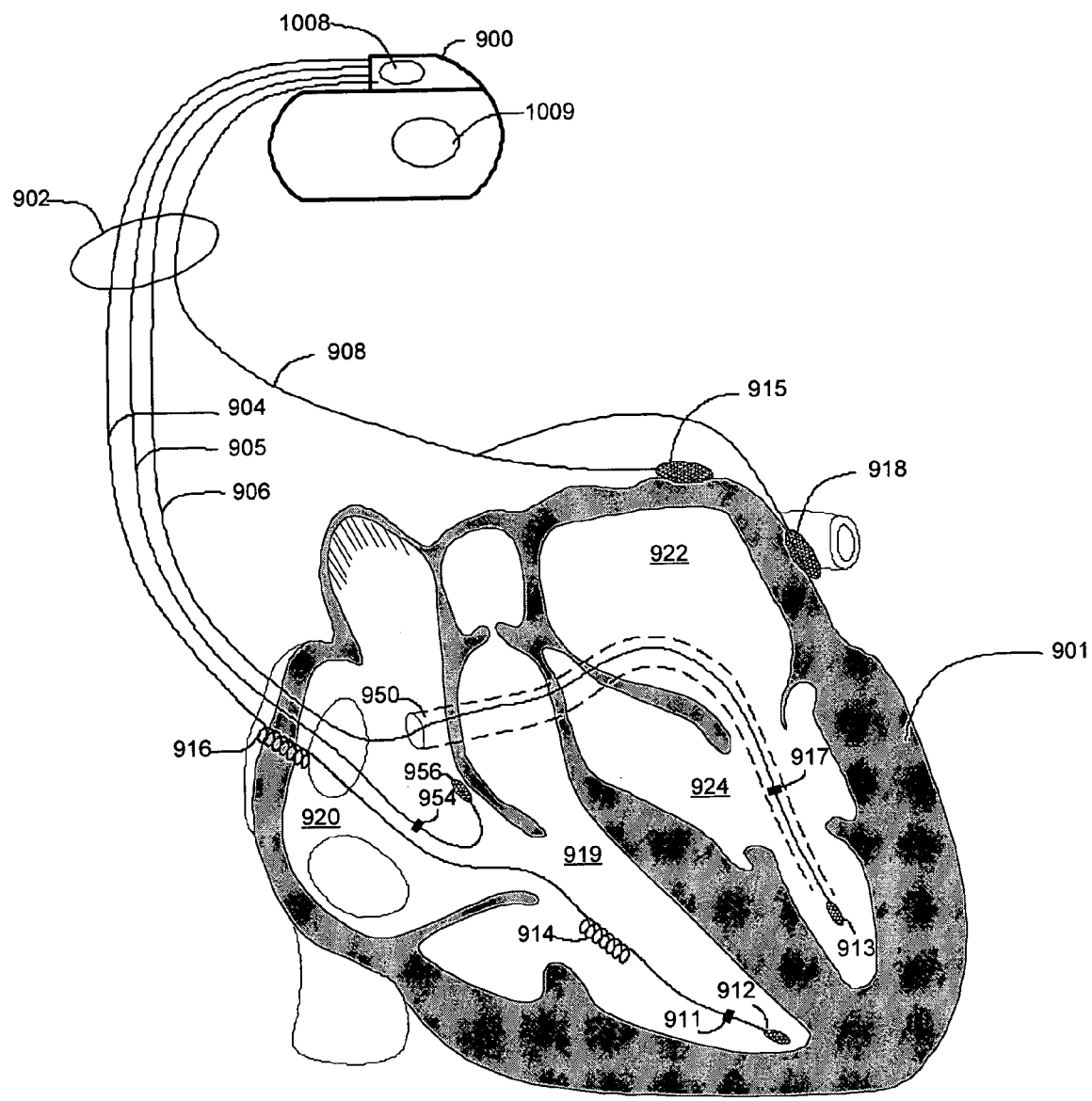
FIG. 9 is a partial view of one embodiment of an implantable medical device in accordance with embodiments of the invention.

Referring now to FIG. 9 of the drawings, there is shown a cardiac rhythm management system that may be used to implement cardiac response classification methods of the present invention. The cardiac rhythm management system in FIG. 9 includes an ICD 900 electrically and physically coupled to a lead system 902. The housing and/or header of the ICD 900 may incorporate one or more electrodes 1008, 1009 used to provide electrical stimulation energy to the heart and to sense cardiac electrical activity. The ICD 900 may utilize all or a portion of the ICD housing as a can electrode 1009. The ICD 900 may include an indifferent electrode positioned, for example, on the header or the housing of the ICD 900. If the ICD 900 includes both a can electrode 1009 and an indifferent electrode 1008, the electrodes 1008, 1009 typically are electrically isolated from each other.

The lead system 902 is used to detect cardiac electrical signals produced by the heart 901 and to provide electrical energy to the heart 901 under certain predetermined conditions to treat cardiac arrhythmias. The lead system 902 may include one or more electrodes used for pacing, sensing, and/or defibrillation. In the embodiment shown in FIG. 9, the lead system 902 includes an intracardiac right ventricular (RV) lead system 904, an intracardiac right atrial (RA) lead system 905, an intracardiac left ventricular (LV) lead system 906, and an epicardiac left atrial (LA) lead system 908. The lead system 902 of FIG. 9 illustrates one embodiment that may be used in connection with the cardiac response classification methodologies described herein. Other leads and/or electrodes may additionally or alternatively be used.

The lead system 902 may include intracardiac leads 904, 905, 906 implanted in a human body with portions of the intracardiac leads 904, 905, 906 inserted into a heart 901. The intracardiac leads 904, 905, 906 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 9, the lead system 902 may include one or more epicardial leads 908 having electrodes, e.g., epicardial electrodes, positioned at locations outside the heart for sensing and pacing one or more heart chambers.

The right ventricular lead system 904 illustrated in FIG. 9 includes a superior vena cava (SVC)-coil 916, a right ventricular (RV)-coil 914, an RV-ring electrode 911, and an RV-tip electrode 912. The right ventricular lead system 904 extends through the right atrium 920 and into the right ventricle 919. In particular, the RV-tip electrode 912, RV-ring electrode 911, and RV-coil electrode 914 are positioned at appropriate locations within the right ventricle 919 for sensing and delivering electrical stimulation pulses to the heart. The SVC-coil 916 is positioned at an appropriate location within the right atrium chamber 920 of the heart 901 or a major vein leading to the right atrial chamber 920 of the heart 901.

In one configuration, the RV-tip electrode 912 referenced to the can electrode 1009 may be used to implement unipolar pacing and/or sensing in the right ventricle 919. Bipolar pacing and/or sensing in the right ventricle may be implemented using the RV-tip 912 and RV-ring 911 electrodes. In yet another configuration, the RV-ring 911 electrode may optionally be omitted, and bipolar pacing and/or sensing may be accomplished using the RV-tip electrode 912 and the RV-coil 914, for example. The right ventricular lead system 904 may be configured as an integrated bipolar pace/shock lead. The RV-coil 914 and the SVC-coil 916 are defibrillation electrodes.

The left ventricular lead 906 includes an LV distal electrode 913 and an LV proximal electrode 917 located at appropriate locations in or about the left ventricle 924 for pacing and/or sensing the left ventricle 924. The left ventricular lead 906 may be guided into the right atrium 920 of the heart via the superior vena cava. From the right atrium 920, the left ventricular lead 906 may be deployed into the coronary sinus ostium, the opening of the coronary sinus 950. The lead 906 may be guided through the coronary sinus 950 to a coronary vein of the left ventricle 924. This vein is used as an access pathway for leads to reach the surfaces of the left ventricle 924 which are not directly accessible from the right side of the heart. Lead placement for the left ventricular lead 906 may be achieved via subclavian vein access and a preformed guiding catheter for insertion of the LV electrodes 913, 917 adjacent to the left ventricle.

Unipolar pacing and/or sensing in the left ventricle may be implemented, for example, using the LV distal electrode referenced to the can electrode 1009. The LV distal electrode 913 and the LV proximal electrode 917 may be used together as bipolar sense and/or pace electrodes for the left ventricle. The left ventricular lead 906 and the right ventricular lead 904, in conjunction with the ICD 900, may be used to provide cardiac resynchronization therapy such that the ventricles of the heart are paced substantially simultaneously, or in phased sequence, to provide enhanced cardiac pumping efficiency for patients suffering from heart failure.

The right atrial lead 905 includes a RA-tip electrode 956 and an RA-ring electrode 954 positioned at appropriate locations in the right atrium 920 for sensing and pacing the right atrium 920. In one configuration, the RA-tip 956 referenced to the can electrode 1009, for example, may be used to provide unipolar pacing and/or sensing in the right atrium 920. In another configuration, the RA-tip electrode 956 and the RA-ring electrode 954 may be used to effect bipolar pacing and/or sensing.

FIG. 9 illustrates one embodiment of a left atrial lead system 908. In this example, the left atrial lead 908 is implemented as an epicardiac lead with LA distal 918 and LA proximal 915 electrodes positioned at appropriate locations outside the heart 901 for sensing and pacing the left atrium 922. Unipolar pacing and/or sensing of the left atrium may be accomplished, for example, using the LA distal electrode 918 to the can 1009 pacing vector. The LA proximal 915 and LA distal 918 electrodes may be used together to implement bipolar pacing and/or sensing of the left atrium 922.

Figure 10A:
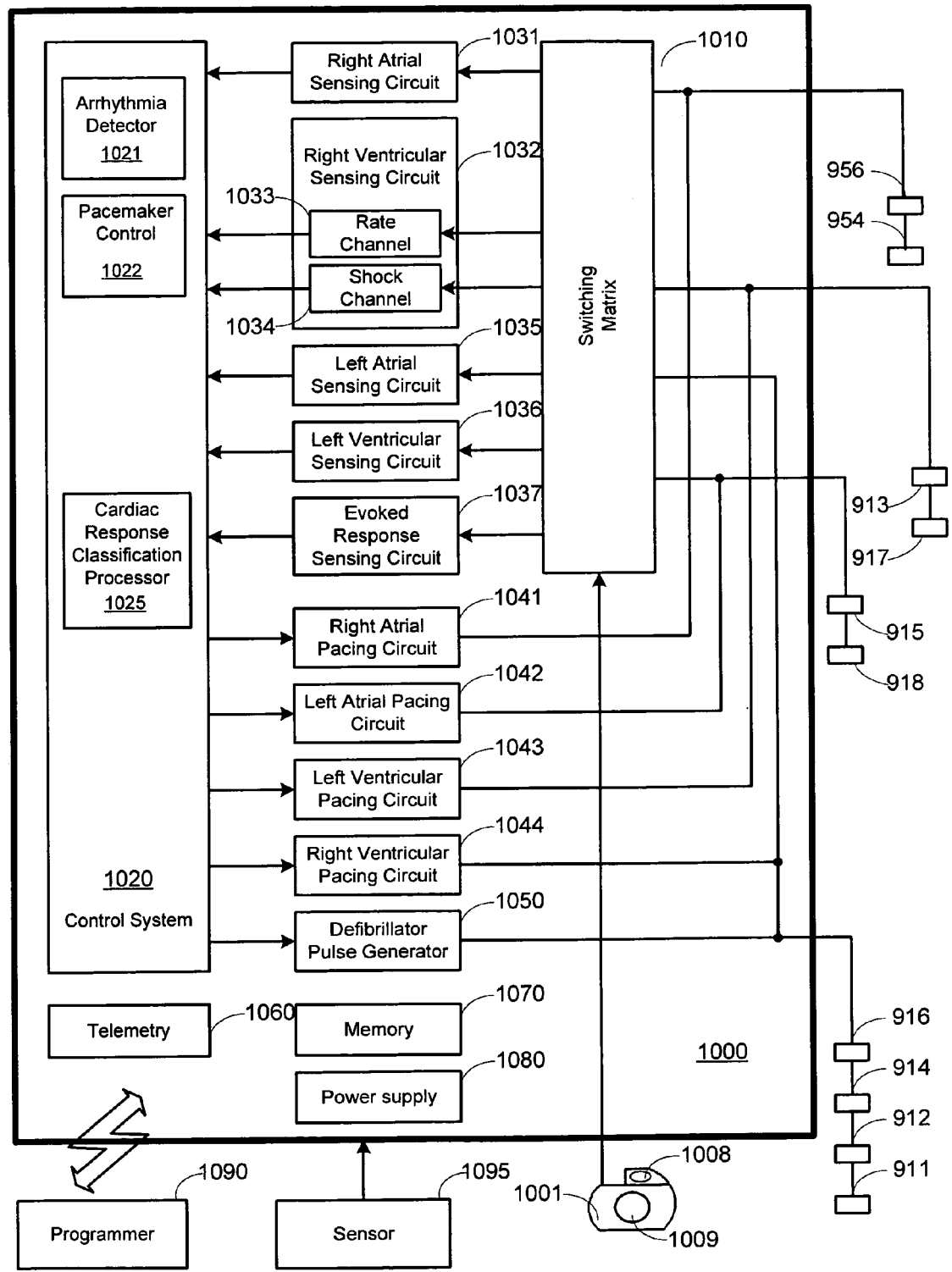
FIG. 10A is a block diagram of an implantable medical device that may be used to classify a cardiac response to pacing in accordance with embodiments of the invention.

Referring now to FIG. 10A, there is shown an embodiment of a cardiac defibrillator 1000 suitable for implementing a cardiac response classification methodology of the present invention. FIG. 10A shows a cardiac defibrillator divided into functional blocks. It is understood by those skilled in the art that there exist many possible configurations in which these functional blocks can be arranged. The example depicted in FIG. 10A is one possible functional arrangement. Other arrangements are also possible. For example, more, fewer or different functional blocks may be used to describe a cardiac defibrillator suitable for implementing the cardiac response classification methodology of the present invention. In addition, although the cardiac defibrillator 1000 depicted in FIG. 10A contemplates the use of a programmable microprocessor-based logic circuit, other circuit implementations may be utilized.

The cardiac defibrillator 1000 depicted in FIG. 10A includes circuitry for receiving cardiac signals from a heart and delivering electrical stimulation energy to the heart in the form of pacing pulses or defibrillation shocks. In one embodiment, the circuitry of the cardiac defibrillator 1000 is encased and hermetically sealed in a housing 1001 suitable for implanting in a human body. Power to the cardiac defibrillator 1000 is supplied by an electrochemical battery 1080. A connector block (not shown) is attached to the housing 1001 of the cardiac defibrillator 1000 to allow for the physical and electrical attachment of the lead system conductors to the circuitry of the cardiac defibrillator 1000.

The cardiac defibrillator 1000 may be a programmable microprocessor-based system, including a control system 1020 and a memory 1070. The memory 1070 may store parameters for various pacing, defibrillation, and sensing modes, along with other parameters. Further, the memory 1070 may store data indicative of cardiac signals received by other components of the cardiac defibrillator 1000. The memory 1070 may be used, for example, for storing historical EGM and therapy data. The historical data storage may include, for example, data obtained from long term patient monitoring used for trending or other diagnostic purposes. Historical data, as well as other information, may be transmitted to an external programmer unit 290 as needed or desired.

The control system 1020 and memory 1070 may cooperate with other components of the cardiac defibrillator 1000 to control the operations of the cardiac defibrillator 1000. The control system depicted in FIG. 10A incorporates a cardiac response classification processor 1025 for classifying cardiac responses to pacing stimulation in accordance with various embodiments of the present invention. The control system 1020 may include additional functional components including a pacemaker control circuit 1022, an arrhythmia detector 1021, along with other components for controlling the operations of the cardiac defibrillator 1000.

If an arrhythmia is detected by the arrhythmia detector 1021, the cardiac defibrillator 1000 may respond by delivering one or more of a variety of therapies to mitigate or terminate the arrhythmia. For example, the cardiac defibrillator may deliver anti-tachycardia pacing via one or more of the pacing circuits 1041-1044, or may delivery one or more high energy shocks to the heart via the defibrillator pulse generator 1050.

Telemetry circuitry 1060 may be implemented to provide communications between the cardiac defibrillator 1000 and an external programmer unit 1090. In one embodiment, the telemetry circuitry 1060 and the programmer unit 1090 communicate using a wire loop antenna and a radio frequency telemetric link, as is known in the art, to receive and transmit signals and data between the programmer unit 1090 and the telemetry circuitry 1060. In this manner, programming commands and other information may be transferred to the control system 1020 of the cardiac defibrillator 1000 from the programmer unit 1090 during and after implant. In addition, stored cardiac data pertaining to capture threshold, capture detection and/or cardiac response classification, for example, along with other data, may be transferred to the programmer unit 1090 from the cardiac defibrillator 1000.

In some embodiments, a sensor 1095 may be coupled to the control system 1020 of the defibrillator 1000. The sensor 1095 may comprise, for example, a transthoracic impedance sensor capable of sensing the patient's respiration, or an accelerometer configured to sense patient activity. The output from the sensor 1095 may be employed by the control system 1020 to adaptively control the pacing rate. Rate adaptive pacing is may be used to modify the pacing rate to accommodate changes in the patient's activity level and/or hemodynamic need.

In the embodiment of the cardiac defibrillator 1000 illustrated in FIG. 10A, electrodes RA-tip 956, RA-ring 954, RV-tip 912, RV-ring 911, RV-coil 914, SVC-coil 916, LV distal electrode 913, LV proximal electrode 917, LA distal electrode 918, LA proximal electrode 915, indifferent electrode 1008, and can electrode 1009 may be coupled through a switch matrix 1010 to sensing circuits 1031-1037.

A right atrial sensing circuit 1031 serves to detect and amplify electrical signals from the right atrium of the heart. Bipolar sensing in the right atrium may be implemented, for example, by sensing voltages developed between the RA-tip 956 and the RA-ring 954. Unipolar sensing may be implemented, for example, by sensing voltages developed between the RA-tip 956 and the can electrode 1009. Outputs from the right atrial sensing circuit are coupled to the control system 1020.

A right ventricular sensing circuit 1032 serves to detect and amplify electrical signals from the right ventricle of the heart. The right ventricular sensing circuit 1032 may include, for example, a right ventricular rate channel 1033 and a right ventricular shock channel 1034. Right ventricular cardiac signals sensed through use of the RV-tip 912 electrode are right ventricular near-field signals and are denoted RV rate channel signals. A bipolar RV rate channel signal may be sensed as a voltage developed between the RV-tip 912 and the RV-ring. Alternatively, bipolar sensing in the right ventricle may be implemented using the RV-tip electrode 912 and the RV-coil 914. Unipolar rate channel sensing in the right ventricle may be implemented, for example, by sensing voltages developed between the RV-tip 912 and the can electrode 1009.

Right ventricular cardiac signals sensed through use of the defibrillation electrodes 914, 916 are far-field signals, also referred to as RV morphology or RV shock channel signals. More particularly, a right ventricular shock channel signal may be detected as a voltage developed between the RV-coil 914 and the SVC-coil 916. A right ventricular shock channel signal may also be detected as a voltage developed between the RV-coil 914 and the can electrode 1009. In another configuration the can electrode 1009 and the SVC-coil electrode 916 may be electrically shorted and a RV shock channel signal may be detected as the voltage developed between the RV-coil 914 and the can electrode 1009/SVC-coil 916 combination. Outputs from the right ventricular sensing circuit 1032 are coupled to the control system 1020.

Left atrial cardiac signals may be sensed through the use of one or more left atrial electrodes 915, 918, which may be configured as epicardial electrodes. A left atrial sensing circuit 1035 serves to detect and amplify electrical signals from the left atrium of the heart. Bipolar sensing and/or pacing in the left atrium may be implemented, for example, using the LA distal electrode 918 and the LA proximal electrode 915. Unipolar sensing and/or pacing of the left atrium may be accomplished, for example, using the LA distal electrode 118 to can vector 1009 or the LA proximal electrode 915 to can vector 1009.

A left ventricular sensing circuit 1036 serves to detect and amplify electrical signals from the left ventricle of the heart. Bipolar sensing in the left ventricle may be implemented, for example, by sensing voltages developed between the LV distal electrode 913 and the LV proximal electrode 917. Unipolar sensing may be implemented, for example, by sensing voltages developed between the LV distal electrode 913 or the LV proximal electrode 917 to the can electrode 1009.

Optionally, an LV coil electrode (not shown) may be inserted into the patient's cardiac vasculature, e.g., the coronary sinus, adjacent the left heart. Signals detected using combinations of the LV electrodes, 913, 917, LV coil electrode (not shown), and/or can electrodes 1009 may be sensed and amplified by the left ventricular sensing circuitry 1036. The output of the left ventricular sensing circuit 1036 is coupled to the control system 1020.

The outputs of the switching matrix 1010 may be operated to couple selected combinations of electrodes 911, 912, 913, 914, 915, 916, 917, 918, 956, 954, 1008, 1009 to an evoked response sensing circuit 1037. The evoked response sensing circuit 1037 serves to sense and amplify voltages developed using various combinations of electrodes for cardiac response classification in accordance with embodiments of the invention.

Various combinations of pacing and sensing electrodes may be utilized in connection with pacing and sensing the cardiac signal following the pace pulse to classify the cardiac response to the pacing pulse. In embodiments described herein, the RV-tip 912 to RV-coil 914 sensing vector, the RV-ring 911 to RV-coil 914 sensing vector, the LV distal electrode 913 to LV coil electrode sensing vector, the LV proximal electrode 917 to LV coil electrode sensing vector, the RA-tip 956 to SVC-coil 916 sensing vector, the RA-ring 954 to SVC-coil 916 sensing vector, the LA distal electrode 918 to LA coil electrode sensing vector (not shown), or the LA proximal electrode 915 to LA coil electrode sensing vector, is used for discriminating non-capture, capture, and non-captured intrinsic beats.

Sensing the cardiac signal following a pacing pulse using the same electrode combination for both pacing and sensing may yield a sensed cardiac signal including a pacing artifact component associated with residual post pace polarization at the electrode-tissue interface. The pacing artifact component may be superimposed on a smaller signal indicative of the cardiac response to the pacing pulse, i.e., the evoked response. The pacing output circuitry may include a coupling capacitor to block DC components from the heart and to condition the pacing stimulus pulse. A relatively large coupling capacitor may cause a larger pacing artifact that decays exponentially over a relatively long period of time.

The presence of a large pacing artifact signal may complicate the classification of the cardiac response to pacing. Various embodiments of the invention are directed to methods involving detection of a cardiac signal following pacing and canceling the pacing artifact from the detected signal. Classification of the cardiac response to pacing is implemented using the pacing artifact cancelled signal. Cancellation of the pacing artifact in cardiac response classification is particularly important when the same or similar electrode combinations are used both for delivering pacing pulses and for sensing the cardiac signals following the delivery of the pacing pulses. Cancellation of the pacing artifact may also be used when a first electrode combination is used for pacing the heart chamber and a different electrode combination is used to sense the subsequent cardiac response. Cancellation of pacing artifacts, aspects of which may be utilized in the capture detection approaches of embodiments described herein, are discussed in commonly owned U.S. patent application Ser. No. 10/335,534, filed on Dec. 31, 2002, which is incorporated herein by reference.

The pacemaker control circuit 1022, in combination with pacing circuitry for the left atrium, right atrium, left ventricle, and right ventricle 1041, 1042, 1043, 1044, may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The cardiac signal following the pacing pulse may be sensed using the same vector or a different vector than that used for delivery of the pacing pulse. In a preferred embodiment, a pacing pulse is delivered to the right ventricle using the RV-tip to RV-ring vector. The cardiac signal following and associated with the pacing pulse is sensed using the RV-tip to RV-coil sensing vector. In this scenario, with a suitable blanking period, the pacing artifact has dissipated substantially from the sensed cardiac signal leaving sufficient signal to determine the cardiac response to the pacing pulse. Alternatively, the pacing artifact cancellation techniques described in commonly owned U.S. Pat. No. 7,162,301 may be utilized to reduce the effect of the pacing artifact.

The cardiac response classification processor 1025 includes circuitry for determining the cardiac response to the pacing pulse. In a preferred embodiment, sensing in the right ventricle is accomplished using the RV-tip 912 and RV-coil 914 electrodes. The cardiac response classification processor 1025 is primarily responsible for implementing the cardiac response classification methodologies described above. Using the above-described processes, the cardiac response classification processor 1025 may classify the cardiac response to pacing as one of a non-captured response, a captured response and a non-captured response and an intrinsic beat as previously described. Cardiac response classification may be accomplished, for example, using multiple classification intervals defined following delivery of the pacing pulse as described in greater detail herein.

FIGS. 10B and 10C illustrate more detailed examples of pacing and sensing circuitry, respectively, that may be used for cardiac pace/sense channels of a pacemaker in accordance with embodiments of the invention. In example embodiments of the invention, the pacing circuit of FIG. 10B includes a power supply or battery 1061, a first switch 1062, a second switch 1064, a pacing charge storage capacitor 1063, coupling capacitor 1065, and a pacer capacitor charging circuit 1069 all of which are cooperatively operable under the direction of a controller of known suitable construction. The power supply or battery 1061 is preferably the battery provided to power the pacemaker and may comprise any number of commercially available batteries suitable for pacing applications. The switches 1062, 1064 may be implemented using any number of conventionally available switches. The pacing capacitor charging circuit 1069 includes circuitry to regulate the voltage across the pacing charge storage capacitor 1063.

The pacing charge storage capacitor 1063 may also comprise any number of conventional storage capacitors that can be used to develop a sufficient pacing charge for stimulating the heart. The primary function of the coupling capacitor 1065 is to block any DC signal from reaching the heart during pacing and additionally to attenuate the polarization voltage or "afterpotential" that results from pacing. The coupling capacitor 1065 may have a capacitance, for example, in the range of about 2 microfarads to about 22 microfarads. Energy stored in the pacing charge storage capacitor 1063 may be delivered to the heart 1068 using various combinations of cardiac electrodes 1066, 1067, as described above.

FIG. 10C illustrates a block diagram of circuit 1099 that may be used to sense cardiac signals following the delivery of a pacing stimulation and classify the cardiac response to the pacing stimulation according to embodiments of the invention. A switch matrix 1084 is used to couple the cardiac electrodes 1071, 1072 in various combinations discussed above to the sensing portion 1070 of the cardiac response classification circuit 1095. The sensing portion 1070 includes filtering and blanking circuitry 1075, 1077, sense amplifier 1085, band pass filter 1081, and analog to digital converter 1082. The analog to digital converter 1082 is coupled to a cardiac response classification processor 1083.

A control system, e.g., the control system 1020 depicted in FIG. 10A, is operatively coupled to components of the cardiac response classification circuit 1025 and controls the operation of the cardiac response classification circuit 1025, including the filtering and blanking circuits 1075, 1077. Following a blanking period of sufficient duration following delivery of the pacing stimulation, the blanking circuitry 1075, 1077 operates to allow detection of a cardiac signal responsive to the pacing stimulation. The cardiac signal is filtered, amplified, and converted from analog to digital form. The digitized signal is communicated to the cardiac response classification processor 1025 which operates to classify cardiac responses to pacing according to the methodologies presented in embodiments of the invention described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of automatically classifying a cardiac response to a pacing pulse and delivering therapy, comprising:
    sensing a cardiac signal associated with the pacing pulse;
    detecting morphological characteristics of the cardiac signal and measuring a feature value of each of the morphological characteristics;
    comparing at least one feature value to at least another feature value;
    selecting, based on comparison of the feature values, one or more of the feature values to use for intrinsic response detection;
    classifying the cardiac response to the pacing pulse including discriminating between capture and non-capture with intrinsic activity based on comparison of the selected one or more feature values to at least one reference value indicative of an intrinsic response; and
    controlling pacing therapy based on the cardiac response to the pacing pulse.

2. The method of claim 1, wherein:
    detecting the morphological characteristics of the cardiac signal comprises detecting first and second peaks having the same polarity;
    selecting the feature values comprises selecting a greater peak magnitude; and
    discriminating between capture and-non-capture with intrinsic activity comprises comparing the selected peak magnitude to a peak reference value indicative of the intrinsic response.

3. The method of claim 1, wherein sensing the cardiac signal comprises sensing the cardiac signal using a defibrillation electrode.

4. The method of claim 1, wherein sensing the cardiac signal comprises sensing the cardiac signal using a right ventricular tip electrode and a right ventricular coil electrode or a right ventricular ring electrode and a right ventricular coil electrode.

5. The method of claim 1, wherein sensing the cardiac signal comprises sensing the cardiac signal using a left ventricular distal electrode and a left ventricular coil electrode or a left ventricular proximal electrode and a left ventricular coil electrode.

6. The method of claim 1, wherein sensing the cardiac signal comprises sensing the cardiac signal using a right atrial tip electrode and a superior vena-cava coil electrode or a right atrial ring electrode and a superior vena-cava coil electrode.

7. The method of claim 1, wherein sensing the cardiac signal comprises sensing the cardiac signal using a left atrial distal electrode and a left atrial coil electrode or a left atrial proximal electrode and a left atrial coil electrode.

8. The method of claim 1, wherein sensing the cardiac signal comprises sensing the cardiac signal following a blanking period, wherein a duration of the blanking period is selected to allow a pacing artifact signal component to dissipate from the sensed cardiac signal.

9. The method of claim 1, further comprising classifying the cardiac response as non-capture if a feature value of a morphological characteristic does not achieve a capture threshold criteria.

10. The method of claim 1, wherein detecting morphological characteristics of the cardiac signal comprises:
    timing a first time interval following the pacing pulse;
    detecting a first morphological characteristic within the first time interval following the pacing pulse;
    timing a second time interval following the first time interval; and
    detecting a second morphological characteristic within the second time interval following the first time interval.

11. The method of claim 10, wherein:
    detecting the first morphological characteristic comprises detecting a first peak of the cardiac signal in the first time interval; and
    detecting the second morphological characteristic comprises detecting a second peak of the cardiac signal in the second time interval.

12. The method of claim 11, wherein:
    selecting the feature values comprises selecting a feature value associated with the first peak or a feature value associated with the second peak; and
    discriminating between capture and non-capture with intrinsic activity comprises comparing the selected one or more feature values to a reference value indicative of the intrinsic response.

13. The method of claim 1, wherein:
    detecting the morphological characteristics of the cardiac signal and measuring a feature value of each of the morphological characteristics comprises:
        detecting a first cardiac signal characteristic in a first time interval and measuring a first feature value of the first cardiac signal characteristic; and
        detecting a second cardiac signal characteristic in a second time interval and measuring a second feature value of the second cardiac signal characteristic;
    comparing at least one feature value with at least another feature value comprises comparing the first feature value with the second feature value;
    selecting the feature values comprises selecting a larger feature value of the first and the second feature values; and
    discriminating between capture and non-capture with intrinsic activity comprises comparing the larger feature value to the reference value indicative of the intrinsic response.

14. The method of claim 13, further comprising:
    determining an average feature value of a plurality of cardiac signals representative of captured cardiac responses; and updating the reference value based on the average feature value.

15. The method of claim 14, wherein determining the average feature value of the plurality of cardiac signals comprises determining a weighted average.

16. A capture detection system configured to classify a cardiac pacing response, comprising:
a plurality of cardiac electrodes configured to electrically couple to a heart;
a sensing system, coupled to the cardiac electrodes and configured to sense a cardiac signal associated with a pacing pulse using the plurality of cardiac electrodes;
a capture detector coupled to the sensing system, the capture detector configured to:
detect morphological characteristics of the cardiac signal;
measure a feature value of each of the morphological characteristics;
compare at least one feature value to at least another feature value;
select, based on comparison of the feature values, one or more of the feature values for use in discriminating between capture and non-capture with intrinsic activity of the cardiac signal;
compare the one or more selected feature values to at least one reference value indicative of intrinsic activity; and
classify the cardiac pacing response to the pacing pulse based on the comparison of the one or more selected feature values to the at least one reference value indicative of intrinsic activity; and
pacing circuitry configured to deliver pacing therapy based on the classification of the cardiac pacing response.

17. The system of claim 16, wherein the capture detector is configured to sense a first characteristic of the cardiac signal in a first time interval and to sense a second characteristic of the cardiac signal in a second time interval.

18. The system of claim 17, wherein one or both of the first and second time intervals are programmable.

19. The system of claim 16, wherein the plurality of cardiac electrodes comprises a right ventricular tip electrode and a right ventricular coil electrode or a right ventricular ring electrode and a right ventricular coil electrode.

20. The system of claim 16, wherein the plurality of cardiac electrodes comprises a left ventricular distal electrode and a left ventricular coil electrode or a left ventricular proximal electrode and a left ventricular coil electrode.

21. The system of claim 16, wherein the plurality of cardiac electrodes comprises a right atrial tip electrode and a superior vena-cava coil electrode or a right atrial ring electrode and a superior vena-cava coil electrode.

22. The system of claim 16, wherein the plurality of cardiac electrodes comprises a left atrial distal electrode and a left atrial coil electrode or a left atrial proximal electrode and a left atrial coil electrode.

23. The system of claim 16, wherein the sensing system is configured to sense the cardiac signal following a blanking period, wherein a duration of the blanking period is selected to allow a majority of a pacing artifact signal component to dissipate from the sensed cardiac signal.

24. The system of claim 16, wherein the capture detector is configured to classify the cardiac response to the pacing pulse as non-capture if a feature value of a first characteristic is not consistent with a capture threshold criteria.

25. The system of claim 24, wherein the capture threshold criteria is based on a weighted average value of previously sensed first characteristics associated with capture.

26. The system of claim 16, wherein the feature values include a first peak value of a first cardiac signal peak occurring in a first time interval and a second peak value of a second cardiac signal peak occurring in a second time interval, the first and second cardiac signal peaks having the same polarity.

27. The system of claim 26, wherein the at least one reference value is based on an average peak value of intrinsic responses.

28. The system of claim 26, wherein the capture detector is configured to select a larger of the first peak value having a first polarity and the second peak value of the same polarity and to discriminate between capture and non-capture with intrinsic activity based on comparison of the larger peak value to the reference value indicative of the intrinsic response.

29. A system for automatically classifying a cardiac response to a pacing pulse, comprising:
means for sensing a cardiac signal associated with the pacing pulse;
means for detecting morphological characteristics of the cardiac signal and measuring a feature value of each of the morphological characteristics;
means for comparing at least one feature value to at least one other feature value;
means for selecting, based on comparison of the feature values, one or more of the feature values to use for intrinsic response detection;
means for classifying the cardiac response to the pacing pulse by discriminating between capture and non-capture with intrinsic activity based on comparison of the selected one or more feature values to at least one reference value indicative of an intrinsic response; and
means for delivering cardiac pacing therapy based on cardiac pacing response classification.

30. The system of claim 29, further comprising means for classifying the cardiac response as non-capture without intrinsic activity if a first feature value does not achieve a threshold level.

31. The system of claim 29, wherein the means for detecting detects a first characteristic of the cardiac signal sensed in a first time interval and detects a second characteristic of the cardiac signal sensed in a second time interval.

32. The system of claim 29, wherein:
the means for detecting detects a first positive peak of the cardiac signal in a first time interval and detects a second positive peak of the cardiac signal in a second time interval;
the means for selecting the feature values selects a larger positive peak value of the first and the second positive peak values; and
the means for discriminating compares the larger positive peak value to the reference value indicative of an intrinsic response and discriminates between capture and non-capture with intrinsic activity based on the comparison.

33. The system of claim 29, further comprising:
means for determining an average peak value of a plurality of captured cardiac response signals; and
means for determining the reference value indicative of an intrinsic response based on the average peak value.

34. The system of claim 29, wherein the reference value indicative of an intrinsic response comprises an average value of intrinsic responses.

* * * * *